(12) United States Patent
Baum et al.

(10) Patent No.: US 6,822,107 B1
(45) Date of Patent: Nov. 23, 2004

(54) CHEMICAL VAPOR DEPOSITION PRECURSORS FOR DEPOSITION OF COPPER

(75) Inventors: Thomas H. Baum, New Fairfield, CT (US); Gautam Bhandari, New York, NY (US); Chongying Xu, New Milford, CT (US)

(73) Assignee: Advanced Technology Materials, Inc., Danbury, CT (US)

(*) Notice: Subject to any disclaimer, the term of this patent is extended or adjusted under 35 U.S.C. 154(b) by 0 days.

(21) Appl. No.: 10/643,272

(22) Filed: Aug. 19, 2003

(51) Int. Cl.[7] .............................. C07F 1/08; C23C 16/00
(52) U.S. Cl. ..................... 556/113; 427/587; 427/593
(58) Field of Search .................... 556/113; 427/587, 427/593

(56) References Cited

U.S. PATENT DOCUMENTS 5,087,609 A * 2/1992 Whitwell et al. ........... 505/446

* cited by examiner

*Primary Examiner*—Porfirio Nazario-Gonzalez
(74) *Attorney, Agent, or Firm*—Margaret Chappuis; Steven J. Hultquist

(57) ABSTRACT

Copper precursors of the formula (I):

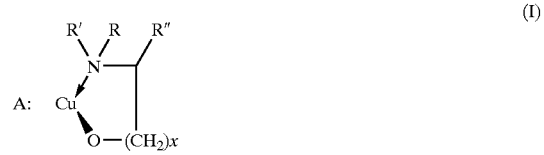

wherein:

Cu is Cu(I) or Cu(II);

x is an integer having a value of from 0 to 4;

each of R, R' and R" may be the same as or different from one another and each is independently selected from the group consisting of H, $C_1$–$C_6$ alky), $C_1$–$C_6$ perfluoroalkyl and $C_6$–$C_{10}$ aryl;

when Cu is Cu(I), A is a Lewis base;

when Cu is Cu(II), A is:

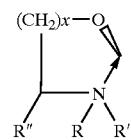

wherein x, R, R' and R" are as specified above.

18 Claims, No Drawings

CHEMICAL VAPOR DEPOSITION PRECURSORS FOR DEPOSITION OF COPPER

FIELD OF THE INVENTION

The present invention relates to the deposition of copper, and to precursor compositions having utility for chemical vapor deposition of copper on substrates, e.g., in the manufacture of semiconductor products.

DESCRIPTION OF THE RELATED ART

Copper is of great interest for use in metallization of very large-scale integration (VLSI) devices, due to its low resistivity, low contact resistance and ability to enhance device performance by reduction in RC time delays. Copper CVD processes suitable for VLSI manufacturing of integrated circuits are extremely valuable to the semiconductor manufacturing industry, but their implementation has been limited by several associated problems of integrating copper into silicon-based devices.

For example, when copper is used for metallization, the deposition on the substrate of an effective diffusion barrier is required, to eliminate deleterious copper-silicon interdiffusion. Another issue in the use of copper is lack of desired long-term electromigration resistance, which can be ameliorated by use of mixed metal alloys, as is done in conventional aluminum metallization, but such technique for enhancing electromigration resistance is also accompanied by loss of the superior electrical properties obtained when pure copper metallization is employed.

In addition to these deficiencies of conventional copper CVD process technology, the copper precursors used or proposed to date are costly, and such high cost constitutes the largest single obstacle to the widespread adoption of copper CVD. Thus, the art has need of copper precursors of relatively low cost, which are thermally stable and have superior transport properties in the CVD process system.

There is therefore a compelling need in the art for new and improved copper precursors.

SUMMARY OF THE INVENTION

The present invention relates to the deposition of copper, and to precursor compositions having utility for chemical vapor deposition of copper on substrates, e.g., in the manufacture of semiconductor products.

In one aspect, the invention relates to a compound of the formula (I):

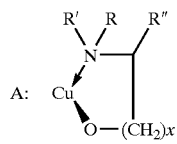

(I)

wherein:
Cu is Cu(I) or Cu(II);
x is an integer having a value of from 0 to 4;
each of R, R' and R" may be the same as or different from one another and each is independently selected from the group consisting of H, $C_1$–$C_6$ alkyl, $C_1$–$C_6$ perfluoroalkyl and $C_6$–$C_{10}$ aryl;

when Cu is Cu(I), A is a Lewis base;
when Cu is Cu(II), A is:

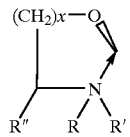

wherein x, R, R' and R" are as specified above.

Another aspect of the invention relates to Cu(I) precursors of the formula (II):

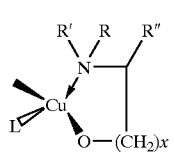

(II)

wherein L is a coordinating Lewis base, and x, R, R' and R" are as defined above.

A further aspect of the invention relates to a copper (I) precursor of formula (III):

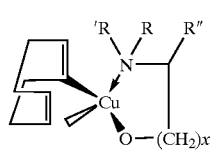

(III)

wherein x, R, R' and R" are as defined above.

Still another aspect of the invention relates to a copper (II) precursor of the formula (IV):

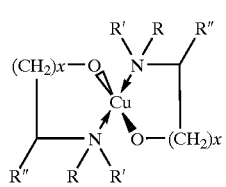

(IV)

wherein x and each of the respective R, R' and R" substituents are as defined hereinabove.

In another aspect, the invention relates to a method of depositing copper on a substrate, comprising contacting the substrate with a vapor of a copper precursor under chemical vapor deposition conditions, wherein the copper precursor comprises a compound of the above formula (I).

Other aspects, features and embodiments of the invention will be more fully apparent from the ensuing disclosure and appended claims.

DETAILED DESCRIPTION OF THE INVENTION AND PREFERRED EMBODIMENTS THEREOF

The present invention is based on the discovery of novel copper precursors that have superior utility for deposition of copper on substrates, e.g., as metallization on such substrates in the manufacture of microelectronic devices or device precursor structures.

The copper precursors of the invention have the general formula (I):

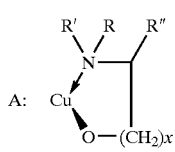
(I)

wherein:

Cu is Cu(I) or Cu(II);

x is an integer having a value of from 0 to 4;

each of R, R' and R" may be the same as or different from one another and each is independently selected from the group consisting of H, $C_1$–$C_1$–$C_6$ alkyl, $C_1$–$C_6$ perfluoroalkyl and $C_6$–$C_{10}$ aryl;

when Cu is Cu(I), A is a Lewis base;

when Cu is Cu(II), A is:

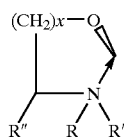

wherein x, R, R' and R" are as specified above.

The invention therefore contemplates Cu(I) precursors of the formula (II):

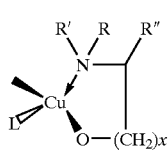
(II)

wherein L is a coordinating Lewis base and wherein x, R, R' and R" are as specified above. The coordinating Lewis base can be of any suitable type, including, without limitation, alkenes, alkynes, dienes, diynes, etc. Preferred Lewis base species include, without limitation, alkene, diene, cycloalkene, cyclodiene, cyclooctadiene, cyclooctatetraene, alkyne, substituted alkyne (symmetrical or asymmetrical), amine, diamine, triamine, tetraamine, ether, diglyme, triglyme, tetraglyme, phosphine, carbonyl, dialkyl sulfide, vinyltrimethylsilane, and allyltrimethylsilane Lewis base species.

A particularly preferred Lewis base copper (I) precursor of the invention is the 1,4-cyclooctadiene-stabilized precursor composition of formula (III):

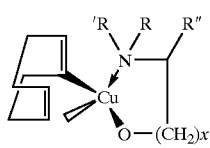
(III)

wherein x, R, R' and R" are as specified above.

The precursor compositions of the invention also include the copper (II) precursors of the formula (IV):

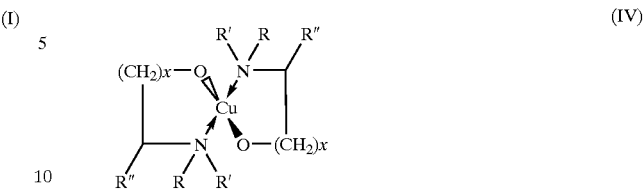
(IV)

wherein each x and each of the respective R. R' and R" substituents are as defined hereinabove.

The compounds of the present invention are readily synthesized by suitable techniques and reaction schemes within the skill of the organometallic chemical synthesis art, without undue experimentation, including but not limited to any one of the following reaction schemes:

(a) $Cu_2O + 2(R'RNCH(CH_2)_xOH) + 2 \ L \rightarrow 2[(R'RNCH(CH_2)_xOH)CuL] + H_2O$ (b) $CuCl.L + (R'RNCH(CH_2)_xONa) \rightarrow [(R'RNCH(CH_2)_xOH)CuL] + NaCl$ (c) $CuCl_2 + 2(R'RNCH(CH_2)_xONa) \rightarrow [(R'RNCH(CH_2)_xOH)]_2Cu + 2NaCl$ The compounds of Formulas I–IV may be provided as liquids (which may be used directly) or solids (which may be used in a solution composition formed by dissolving the solid precursor(s) in a suitable solvent medium that provides for long-term stability).

The compounds of the present invention are advantageously volatilized to form precursor vapor for contacting under CVD process conditions with substrates to deposit copper thereon. The substrate for such purpose can comprise a semiconductor substrate, on which the deposited copper forms a metallization element on the substrate, e.g., an address line of an integrated circuit structure.

In a further embodiment, the copper precursors of the invention can be employed to form copper-containing multicomponent films on substrates, by concurrent chemical vapor deposition of components other than copper, from corresponding source reagent compounds or complexes.

In the compounds of the general formula (I) above, the $C_1$–$C_6$alkyl substituents can be of any suitable type having such carbon numbers, with methyl, isopropyl, and tertiary butyl (t-butyl) being most preferred. Perfluoroalkyl substituents can be correspondingly constituted of any suitable fluoro-substituted alkyl species of such carbon number. Aryl species include any suitable $C_6$–$C_{10}$ aryl species, e.g., phenyl, naphthyl, indolyl, etc., with phenyl being most preferred.

The substituent groups (R R' and R" groups) and Lewis base coordination species of compositions of the invention can be tailored to provide a precursor composition having specific desired, thermal stability, volatilization and transport characteristics for the intended CVD application. The specific CVD process conditions can be widely varied in respective of temperature, pressure, flow rate of precursor and optional carrier gas, and concentration (partial pressure) of precursor vapor in the CVD) reactor chamber, etc., as is readily determinable without undue effort by those skilled in the art, based on the disclosure herein, by selective empirical variation of specific process conditions and analysis of the resulting copper material deposited on the substrate.

The following synthesis example, includes synthesis of $Cu(II)(MeCHOCH_2NMe_2)_2$ and is representative of one specific embodiment of the invention and is not intended to limit the scope of the invention or claims hereto. The synthesis was carried out under a steady flow of nitrogen.

EXAMPLE 1

Synthesis of Cu(II)(MeCHOCH$_2$NMe$_2$)$_2$: All operations were handled under nitrogen using Schlenk techniques. A 250 mL Schlenk flask was charged with 10 g (97 mmol) of Me$_2$NCH$_2$CH(OH)Me, 50 mL of dry THF and a stir bar. Then, 2.33 g (~100 mmol) of NaH was added into the solution slowly. Hydrogen evolution (bubbling) was observed immediately. Upon the completion of addition, the mixture was stirred for three more hours. The resulting solution was slightly brown yellow. Then 6.5 g of CuCl$_2$ (anhydrous) was slowly added into the above-prepared solution. Upon completion of the addition of CuCl$_2$, the purple slurry was stirred at room temperature over night. The mixture was pumped to dryness. Then an organic solvent (e.g., toluene in this case) was used to extract the mixture. After filtration and evaporation of the solvent, a purple solid product was obtained. Further purification through sublimation (temperature 70–90° C. and pressure 50 mtorr) gives a purple crystalline material at over 50% yield.

Similarly, the Cu(I)(MeCHOCH$_2$NMe$_2$).L can be prepared in the procedure described above by replacing CuCl$_2$ with Cu(I)Cl.L$_x$, (where L=neutral Lewis base Ligand and x=0 or 1).

While the invention has been described herein with reference to specific features, aspects, and embodiments, it will be recognized that the invention is not thus limited, but is susceptible of implementation in other variations, modifications and embodiments. Accordingly, the invention is intended to be broadly construed to encompass all such other variations, modifications and embodiments, as being within the scope of the invention hereinafter claimed.

What is claimed is:

1. A compound of formula (I):

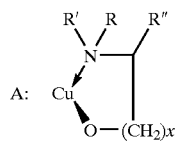

(I)

wherein:

Cu is Cu(I) or Cu(II);

x is an integer having a value of from 0 to 4;

each of R, R' and R" may be the same as or different from one another and each is independently selected from the group consisting of H, C$_1$–C$_6$ alkyl, C$_1$–C$_6$ perfluoroalkyl and C$_6$–C$_{10}$ aryl;

when Cu is Cu(I), A is a Lewis base;

when Cu is Cu(II), A is:

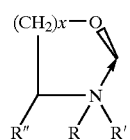

wherein x, R, R' and R" areas specified above, with the proviso that when Cu is Cu(II) and each of R, R' and R" is H, x is not equal to 1.

2. A compound of formula (I):

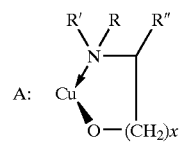

(I)

wherein:

Cu is Cu(I);

x is an integer having a value of from 0 to 4, each of R, R' and R" may be the same as or different from one another and each is independently selected from the group consisting of H, C$_1$–C$_6$ alkyl, C$_1$–C$_6$ perfluoroalkyl and C$_6$–C$_{10}$ aryl;

A is a Lewis base.

3. The copper precursor of claim 2, wherein the Lewis base is selected from the group consisting of alkenes, alkynes, dienes and diynes.

4. The copper precursor of claim 2, wherein the Lewis base is selected from the group consisting of alkene, diene, cycloalkene, cyclodiene cyclooctadiene, cyclooctatetraene, alkyne, substituted alkyne (symmetrical or asymmetrical), amine, diamine, triamine, tetraamine, ether, diglyme, triglyme, tetraglyme, phosphine, carbonyl, dialkyl sulfide, vinyltrimethylsilane, and allyltrimethylsilane.

5. A copper precursor of the formula (II):

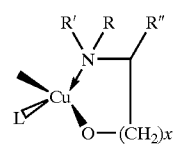

(II)

wherein:

x is an integer having a value of from 0 to 4;

each of R, R' and R" may be the same as or different from one another and each is independently selected from the group consisting of H, C$_1$–C$_6$ alkyl, C$_1$–C$_6$ perfluoroalkyl and C$_6$–C$_{10}$ aryl; and L is a Lewis base coordination species.

6. The copper precursor of claim 5, wherein the Lewis base coordination species is selected from the group consisting of alkenes, alkynes, dienes and diynes.

7. The copper precursor of claim 5, wherein the Lewis base coordination species is selected from the group consisting of alkene, diene, cycloalkene, cyclodiene, cyclooctadiene, cyclooctatetraene, alkyne, substituted alkyne (symmetrical or asymmetrical), amine, diamine, triamine, tetraamine, ether, diglyme, triglyme, tetraglyme, phosphine, carbonyl, dialkyl sulfide, vinyltrimethylsilane, and allyltrimethylsilane.

8. A copper (I) precursor of formula (III):

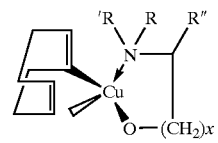

(III)

wherein:

x is an integer having a value of from 0 to 4; and each of R, R' and R" may be the same as or different from one another and each is independently selected from the group consisting of H, $C_1$–$C_6$ alkyl, $C_1$–$C_6$ perfluoroalkyl and $C_6$–$C_{10}$ aryl.

9. A copper (II) precursor of formula (IV):

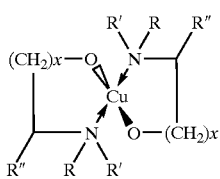
(IV)

wherein:

x is an integer having a value of from 0 to 4; and each of R, R' and R" may be the same as or different from one another and each is independently selected from the group consisting of H, $C_1$–$C_6$ alkyl, $C_1$–$C_6$ perfluoroalkyl and $C_6$–$C_{10}$ ary, with the proviso that if each of R, R' and R" is H, then x is not equal to 1.

10. A method of depositing copper on a substrate, comprising contacting the substrate with a vapor of a copper precursor under chemical vapor deposition conditions, wherein the copper precursor comprises a copper precursor of formula (I):

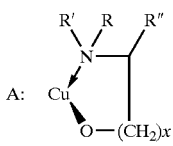
(I)

wherein:

Cu is Cu(I) or Cu(II);

x is an integer having a value of from 0 to 4;

each of R, R' and R" may be the same as or different from one another and each is independently selected from the group consisting of H, $C_1$–C6 alkyl, $C_1$–$C_6$ perfluoroalkyl and $C_6$–$C_{10}$ aryl;

when Cu is Cu(I), A is a Lewis base;

when Cu is Cu(II), A is:

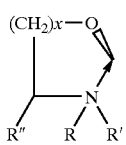

11. The method of claim 10, wherein Cu is Cu(I).

12. The method of claim 11, wherein the Lewis base is selected from the group consisting of alkenes, alkynes, dienes and diynes.

13. The method of claim 11, wherein the Lewis base is selected from the group consisting of alkene, diene, cycloalkene, cyclodiene, cyclooctadiene, cyclooctatetraene, alkyne, substituted alkyne (symmetrical or asymmetrical), amine, diamine, triamine, tetraamine, ether, diglyme, triglyme, tetraglyme, phosphine, carbonyl, dialkyl sulfide, vinyltrimethylsilane, and allyltrimethylsilane.

14. The method of claim 10, wherein the copper precursor has the formula (II):

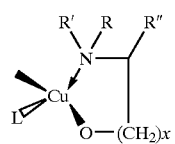
(II)

wherein:

x is an integer having a value of from 0 to 4;

each of R, R' and R" may be the same as or different from one another and each is independently selected from the group consisting of H, $C_1$–$C_6$ alkyl, $C_1$–$C_6$ perfluoroalkyl and $C_6$–$C_{10}$ aryl; and L is a Lewis base coordination species.

15. The method of claim 14, wherein the Lewis base coordination species is selected from the group consisting of alkenes, alkynes, dienes and diynes.

16. The method of claim 14, wherein the Lewis base coordination species is selected from the group consisting of alkene, diene, cycloalkene, cyclodiene, cyclooctadiene, cyclooctatetraene, alkyne, substituted alkyne (symmetrical or asymmetrical), amine, diamine, triamine, tetraamine, ether, diglyme, triglyme, tetraglyme, phosphine, carbonyl, dialkyl sulfide, vinyltrimethylsilane, and allyltrimethylsilane.

17. The method of claim 10, wherein the copper precursor has the formula (III):

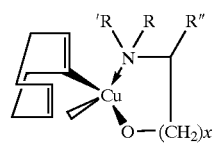
(III)

wherein:

x is an integer having a value of from 0 to 4; and each of R, R' and R" may be the same as or different from one another and each is independently selected from the group consisting of H, $C_1$–$C_6$ alkyl, $C_1$–$C_6$ perfluoroalkyl and $C_6$–$C_{10}$ aryl.

18. The method of claim 10, wherein the copper precursor has the formula (IV):

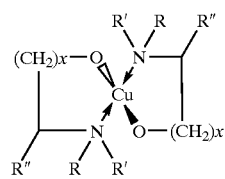
(IV)

wherein:

x is an integer having a value of from 0 to 4; and each of R, R' and R" may be the same as or different from one another and each is independently selected from the group consisting of H, $C_1$–$C_6$ alkyl, $C_1$–$C_6$ perfluoroalkyl and $C_6$–$C_{10}$ aryl.

* * * * *